United States Patent [19]

Donnell

[11] 3,991,112
[45] Nov. 9, 1976

[54] METHYLATED MUCONIC ACID HYDRAZIDES

[75] Inventor: Anne R. Donnell, Springfield, Pa.

[73] Assignee: Sun Research and Development Co., St. Davids, Pa.

[22] Filed: June 23, 1970

[21] Appl. No.: 49,176

[52] U.S. Cl.............................. 260/561 H; 71/113; 71/118; 260/45.85 T; 260/45.9 NC; 260/534 R

[51] Int. Cl.² ................ C07C 103/133; A01N 9/20
[58] Field of Search ..................... 260/534 R, 561 H

[56] References Cited
UNITED STATES PATENTS

| | | | |
|---|---|---|---|
| 3,061,642 | 10/1962 | Weisse et al. ................. | 260/561 H |
| 3,383,289 | 5/1968 | Raymond et al. ................ | 195/30 |
| 3,440,158 | 4/1969 | Suld ................................ | 204/158 |
| 3,450,673 | 6/1969 | McKellys ...................... | 260/561 H |

OTHER PUBLICATIONS

Mar. "Advanced Organic Chemistry", McGraw–Hill Co. (1968), p. 590.
Mar. "Adv. Organic Chemistry", McGraw Hill Book Co. (1968) p. 313.
Chem. Abs. vol. 51, 1957 col. 2596h., Milas et al.

*Primary Examiner*—Anton H. Sutto
*Attorney, Agent, or Firm*—J. Edward Hess; Donald R. Johnson; Stanford M. Back

[57] ABSTRACT

Mono and dihydrazides of the cis-cis, cis-trans and trans-trans isomers of methylated muconic acids including α-methylmuconic acid, β-methylmuconic acid, α,α'-dimethylmuconic acid, α,β'-dimethylmuconic acid, α,α',β-trimethylmuconic acid, α,β,β'-trimethylmuconic acid and α,α',β,β'-tetramethylmuconic acid. The compounds are suitable for use in rubber stabilization, rubber curing and plant growth regulation.

1 Claim, No Drawings

METHYLATED MUCONIC ACID HYDRAZIDES

CROSS REFERENCE TO RELATED APPLICATIONS

The present application is related to commonly owned application of Jackson S. Boyer and Richard D. Cassar Ser. No. 49,178, now abandoned, which discloses the use of certain mono and dihydrazides of organic acids as rubber vulcanization accelerators as well as stabilization of oil extended rubber compositions; also, this application is related to commonly-owned application of Jackson S. Boyer and Richard D. Cassar Ser. No. 49,177, now as U.S. Pat. No. 3,781,628 which discloses the use of certain mono and dihydrazide derivatives of organic acids as viscosity stability improving additives for certain elastomer compositions, both applications being filed of even date herewith.

BACKGROUND OF THE INVENTION

Recent advances in microbiological synthesis of organic acids from petroleum substrates has provided commercially feasible methods for high volume economical production of methylated muconic acids. Specifically, U.S. Pat. No. 3,383,289 issued May 14, 1968 to Richard L. Raymond and Virginia W. Jamison and U.S. Pat. No. 3,440,158 issued Apr. 28, 1969 to George Suld disclose methods for preparing methylated muconic acids and their hydrocarbyl esters. Concurrently, the need for new plant growth regulators has been expressed by the horticultural industry. Also, there is a growing need for new processing and stabilizing additives for use in elastomeric compositions. A new group of chemical compositions which have been found to have utility in plant growth regulation as well as in rubber processing has now been discovered.

DESCRIPTION OF THE INVENTION

It has now been discovered that certain derivatives of methylated muconic acids, namely, the mono and dihydrazides of methylated muconic acids and their hydrocarbyl esters, are particularly effective as plant growth regulating compositions when applied to growing plants. These hydrazide derivatives of methylated muconic acids are also particularly useful as cure activators for unvulcanized elastomeric compositions and as stabilizers for oil extended unvulcanized elastomeric compositions.

The preferred compositions of the present invention are the polymethylated muconic acid hydrazides. Polymethylated muconic acid hydrazides have at least two methyl substituents on two separate carbon atoms of the muconic acid backbone exclusive of the carboxyl groups at each end of the muconic acid molecule.

Particularly preferable of the new compositions of the present invention are the cis-cis, cis-trans and trans-trans isomers of $\alpha,\alpha'$-dimethylmuconic mono and dihydrazide, $\alpha,\beta'$-dmethylmuconic mono and dihydrazide, $\alpha,\alpha',\beta$-trimethylmuconic mono and dihydrazide, $\alpha,\beta,\beta'$-trimethylmuconic mono and dihydrazide and $\alpha,\alpha',\beta,\beta'$-tetramethylmuconic mono and dihydrazide and mixtures thereof.

As previously stated methylated muconic acids have been heretofore disclosed in the art. In particular, methods of preparing and recovering methylated muconic acids and their hydrocarbyl esters are specifically disclosed in U.S. Pat. Nos. 3,383,289 and 3,440,158 noted above. The preparation of each of the isomeric forms of $\alpha,\alpha'$-dimethylmuconic acid has also been described in the prior art by Elvidge, et al., *J. Chem. SOC.*, pages 1026–1033 (1952). These sources show that oxidation of p-xylenol by means of peracetic acid gave a cis-cis form of the acid. The other isomeric forms were obtained indirectly by conversion of the cis-cis form. Also, dimethyl esters of each of the three isomeric forms were prepared by shaking the respective dimethylmuconic acid with ethereal diazomethane. The cis-cis form of polymethylated muconic acids can also be obtained by biological oxidation of p-xylene utilizing special strains of microorganisms as disclosed in U.S. Pat. No. 3,383,289 to Raymond and Jamison noted above.

Procedures for recovering esters of the three isomeric forms of methylated muconic acids usuable in preparing the dihydrazide compositions of the present invention are also disclosed in U.S. Pat. No. 3,440,158 also noted above.

Methylated muconic acids and muconates suitable for use in preparation of the mono and dihydrazide compositions of the present invention include $\alpha$-methylmuconic acid, $\beta'$-methylmuconic acid, $\alpha,\alpha'$-dimethylmuconic acid, $\alpha,\beta$-dimethylmuconic acid, $\alpha,\alpha',\beta$-trimethylmuconic acid, $\alpha,\beta,\beta'$-trimethylmuconic acid, $\alpha,\alpha',\beta,\beta'$-tetramethylmuconic acid and/or monoesters of each of the above-named methylated muconic acids wherein one carboxyl group is attached to a $C_1$ to $C_{20}$ hydrocarbyl radical or their diesters wherein each carboxyl group is attached to a $C_1$ to $C_{20}$ hydrocarbyl radical and mixtures thereof.

$C_1$ to $C_{20}$ hydrocarbyl esters of methylated muconic acids suitable for use in preparing the mono and dihydrazide compositions of the present invention are selected from the hydrocarbyl radicals of $C_1$ to $C_{20}$ hydrocarbons having acyclic, cyclic and aromatic structures such as those disclosed in the text *HANDBOOK OF HYDROCARBONS*, S. W. Ferris, Academic Press Inc., N. Y., (1955), 145 to 249 all of which are incorporated therein by reference. Preferred esters suitable for use in preparing the dihydrazide compositions of the present invention include the $C_1$ to $C_{10}$ hydrocarbyl mono and diesters of the methylated muconic acids hereinabove disclosed. Examples of $C_1$ to $C_{10}$ hydrocarbyl groups include methyl, ethyl, butyl, pentyl, hexyl, heptyl, octyl, nonyl, decyl, cyclopentyl, methylcyclopentyl, dicyclopentyl, cyclohexyl, phenyl, tolyl, xylyl, naphthyl, tetrahydronaphthyl, as well as various isomers of each and mixtures of all.

Examples of some of the esters of the polymethylated muconic acids suitable for use in preparation of the dihydrazide compositions of the present invention include mono and dimethyl esters of $\alpha$-methylmuconic acid, the mono and dimethyl esters of $\beta$-methylmuconic acid, the mono and dimethyl esters of $\alpha,\alpha'$-dimethylmuconic acid, the mono and dimethyl esters of $\alpha,\beta'$-dimethylmuconic acid, the mono and diphenyl esters of $\alpha,\alpha'$-$\beta,\beta'$-tetramethylmuconic acid, the mono and dinaphthyl esters of $\alpha,\beta,\beta'$-trimethylmuconic acid, the mono and di-5,6-diethylacenaphthyl esters of $\alpha,\alpha'$-dimethylmuconic acid, the mono and dicyclohexyl ester of $\alpha,\alpha'$-dimethylmuconic acid, the mono and di-1,2-dimethylcycloheptyl esters of $\alpha,\beta'$-dimethylmuconic acid, the mono and didecahydronaphthyl esters of $\alpha,\alpha',\beta,\beta'$-tetramethylmuconic acid, the mono and di-1,3-dipropylbenzyl esters of $\alpha,\alpha'$-dimethylmuconic acid, the mono and di-2,9-dimethyl-4,7-diisobutyldecyl esters of α,α',β-trimethylmuconic acid, the mono and dianthracyl esters of α,β'-dimethylmuconic acid, mono and di-2,6,10-trimethyl decyl esters of α,α',β,β'-tetramethylmuconic acid and the nonyl ethyl esters of α,α', β, β'-tetramethylmuconic acid.

Preparation of the monohydrazide of a polymethylated muconic acid is accomplished by stoichiometrically adding the amount of hydrazine necessary to provide the monohydrazide of the diacid. This procedure normally provides a mixture of the acid, the dihydrazide and the monohydrazide products each of which occurs as a solid having a separate, distinctive melting point. The monohydrazide can thereafter be recovered from the mixture by solvent extraction and recrystallization.

As one example of the polymethylated muconic acid hydrazide compositions of the invention herein disclosed, the three isomeric forms of the dihydrazide of α,α'-dimethylmuconic acid can be illustrated as follows:

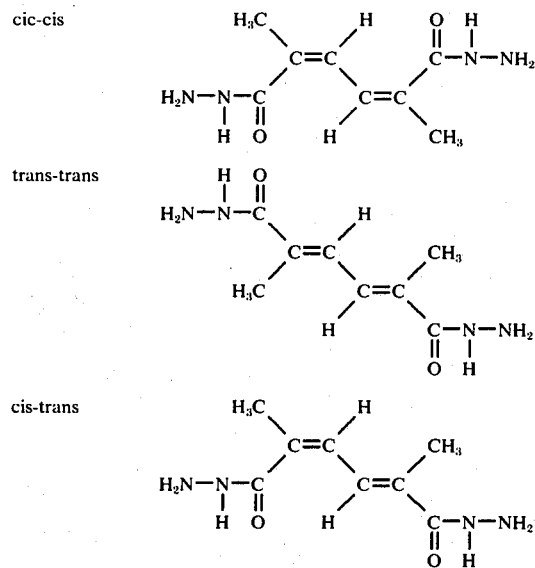

One method of preparation of the dihydrazide of a methylated muconic acid comprises admixing a solution of the methylated muconic acid with a stoichiometric quantity of hydrazine and recovering crystals of the dihydrazide product. The reaction can be illustrated as follows using α,α'-dimethylmuconic acid as a starting material.

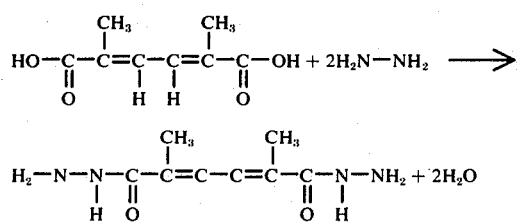

This reaction can be effected at a temperature in the range of 5° to 50° C. with a temperature in the range of 20° to 35° C. being preferred. The rate of the reaction is dependent partially upon the solubility of the reactants in the liquid reaction medium used. The crystalline dihydrazide product can be recovered by filtering or any of the other well-known standard procedures used for recovering solids from liquids. The mono and/or dihydrazides of methylated muconic acids can be prepared from any isomers of the acid or from the mono or diesters of the acids, preparation from the ester form being preferred.

For purposes of general definition, the methylated muconic acid hydrazide composition of the present invention can be defined by the following structured formula:

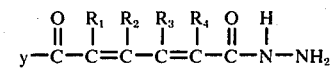

wherein y is selected from —NHNH$_2$, OH and C$_1$ to C$_{20}$ hydrocarbyl radicals and wherein R$_1$, R$_2$, R$_3$ and R$_4$ are selected from hydrogen and —CH$_3$ with at least one R being —CH$_3$.

The preferred compositions of the present invention are polymethylated muconic acid dihydrazides. Referring to the structural formula, the dihydrazides of polymethylated muconic acid wherein R$_1$ and R$_4$ are methyl groups and R$_2$ and R$_3$ are hydrogen radicals is normally referred to as the dihydrazide of α,α'-dimethylmuconic acid. In the instance where the monohydrazide of methylmuconic acid is prepared from the acid form, y of the structural formula is OH. In the instance where the mono hydrazide is prepared from a C$_1$ to C$_{20}$ hydrocarbyl diester of a methylated muconic acid, y is a C$_1$ to C$_{20}$ hydrocarbyl radical.

EXAMPLE I

The dihydrazide of cis-cis α,α'-dimethylmuconic acid was prepared by the following procedure:

A 400 milliliter solution of methanol containing 35 grams of cis-cis α,α'-dimethylmuconic acid dissolved therein was admixed with 200 milliliters of methanol containing 35 grams of hydrazine hydrate. The solution was agitated for one hour at a temperature of 40° C. and thereafter permitted to cool to room temperature. After 72 hours a white crystalline precipitate was recovered from the solution. The recovered product was identified to have a melting point of 204.4° C. and began decomposing at 220° C. Infrared analysis confirmed the structure of the compound to be the dihydrazide of the cis-cis isomer of α,α'-dimethylmuconic acid.

EXAMPLE II

The dihydrazide of trans-trans α,α'-dimethylmuconic acid was prepared as follows:

One hundred milliliters of methanol containing 20 grams of the dimethyl ester of trans-trans α,α'-dimethylmuconic acid were admixed with 300 milliliters of methanol containing 50 grams of hydrazine hydrate and the resulting admixture was agitated and maintained at a temperature of 40° C. for one hour. The mixture was thereafter cooled to room temperature. After 24 hours a white crystalline precipitate was recovered from the solution and characterized as having a melting point of 188° C. and began decomposing at 216° C. Infrared analysis confirmed the structure of the compound as being the dihydrazide of the trans-trans isomer of α,α'-dimethylmuconic acid.

EXAMPLE III

The dihydrazide of cis-cis α,β'-dimethylmuconic acid is prepared by a procedure like that in Example I with the exception that 40 grams of cis-cis α,β'-dimethylmuconic acid are substituted for the α,α'-dimethylmuconic acid. Infrared analysis of the crystalline precipitate recovered from this procedure confirms the product to be the dihydrazide of cis-cis α,β'-dimethylmuconic acid.

EXAMPLE IV

The dihydrazide of cis-cis α,α',β-trimethylmuconic acid is prepared by a procedure like that in Example I with the exception that 40 grams of cis-cis α,α',β-trimethylmuconic acid are substituted for the α,α'-dimethylmuconic acid. Infrared analysis of the crystalline precipitate recovered from this procedure confirms the product to be the dihydrazide of α,α',β-trimethylmuconic acid.

EXAMPLE V

The dihydrazide of trans-trans α,β,β'-trimethylmuconic acid is prepared by a procedure like that in Example II with the exception that 20 grams of the dimethyl ester of trans-trans α,β,β'-trimethylmuconic acid are substituted for the dimethyl ester of α,α'-dimethylmuconic acid. Infrared analysis of the crystalline precipitate recovered from this procedure confirms the product to be the dihydrazide of trans-trans α,β,β'-trimethylmuconic acid.

EXAMPLE VI

The dihydrazide of cis-trans α,α',β,β'-tetramethylmuconic acid is prepared by a procedure like that in Example I with the exception that 40 grams of cis-trans α,α',β,β'-tetramethylmuconic acid are substituted for the α,α'-dimethylmuconic acid. Infrared analysis of the crystalline precipitate recovered from this process confirms the product to be the dihydrazide of cis-trans α,α',β,β'-tetramethylmuconic acid.

EXAMPLE VII

The dihydrazide of α-methylmuconic acid is prepared by the procedure disclosed in Example I with the exception that 40 grams of α-methylmuconic acid is substituted for α,α'-dimethylmuconic acid of Example I. Infrared analysis of the crystalline precipitate recovered from this process confirms the product to be the dihydrazide of α-methylmuconic acid.

EXAMPLE VIII

The dihydrazide of β-methylmuconic acid is prepared by the procedure disclosed in Example I with the exception that 60 grams of the dimethyl ester of β-methylmuconic acid is substituted for the α,α'-dimethylmuconic acid of Example I. Infrared analysis of the crystalline precipitate recovered from this process confirms the product to be the dihydrazide of β-methylmuconic acid.

The examples given herein demonstrate one procedure by which the dihydrazide derivatives of muconic acids and/or $C_1$ to $C_{20}$ hydrocarbyl esters and in particular any of the cis-cis, cis-trans or trans-trans isomers of the various polymethylated muconic acids can be prepared. The dihydrazide derivatives of other methylated muconic acids and their hydrocarbyl esters can be prepared by the same procedures with substantially equivalent results being obtained.

The novel hydrazides of the present invention have been discovered to be useful in the area of plant growth regulation. These compounds have also been shown to be particularly useful as stabilizers for unvulcanized elastomer compositions and as activators in the vulcanization process of certain elastomer compositions. The dihydrazides and monohydrazides of polymethylated muconic acids are particularly effective for use as activators in the vulcanization of natural and synthetic elastomeric compositions and in extending unvulcanized elastomeric compositions with aromatic petroleum hydrocarbon oils. These uses for the present hydrazides as well as other hydrazides are disclosed and claimed in the aforesaid applications of Boyer and Cassar.

In many circumstances when rubber, either natural or synthetic, has been extended with aromatic petroleum hydrocarbon oils and thereafter stored, the composition often suffers a decrease in viscosity and becomes more fluid. In the rubber art this phenomena is normally referred to as "souping". Thus in many circumstances rubber compositions extended with aromatic petroleum hydrocarbon oils cannot be stored for any appreciable length of time because of the "souping" which occurs during such storage. The addition of one or more of the dihydrazides of methylated muconic acids to aromatic hydrocarbon oil extended rubber compositions substantially inhibits "souping" of those rubber compositions. In order to illustrate this type of utility, Examples IX–XIII are presented below.

EXAMPLE IX

Five hundred grams of a styrene-butadiene copolymer synthetic rubber containing approximately 15% polymerized styrene and having a Moony viscosity of 130 was blended on a standard rubber mill with 200 grams of an aromatic petroleum hydrocarbon rubber extending oil characterized as having:

Viscosity at 210° F. of 120
Viscosity at 100° F. of 6,700
Gravity at 60° F. of 10.5
Pour Point of +50
Molecular Weight of 400
Analine Point of 115
Aromatics Content of 81 wt.%
Ca — 40%
Cn — 26%
Cp — 34%
Flash Point of 440° F.
Fire Point of 410° F.
Viscosity Gravity Constant of 0.946

This blended rubber composition was then placed in a hot air circulating oven at 225° F. for a period of 30 hours. Prior to this aging treatment, the Moony viscosity on the blended composition was determined at 212° F. and was found to be 40. After the 30 hours of aging, a final Moony viscosity on the same composition was found to be less than 10.

EXAMPLE X

A composition identical to that disclosed in Example IX was prepared with the exception that prior to blending the oil with the rubber on the rubber mill 2½ grams of the dihydrazide of trans-trans-α,α'-dimethylmuconic acid were dispersed in the aromatic oil. The blended composition of rubber extending oil and dihydrazide had a Moony viscosity at 212° F. of 40. The composition after being aged for 30 hours in a hot air circulating oven maintained at 225° F. was then again evaluated for Moony viscosity and found to have a viscosity of 39 which in effect was substantially no change from the original viscosity.

Thus a comparison of the results of Example IX with those obtained in Example X illustrates the effect achieved by the addition of the dihydrazide of a dimethylmuconic acid to an oil extended styrene-butadiene copolymer rubber composition aged in a hot air circulating oven.

EXAMPLE XI

The dihydrazide of cis-cis-$\alpha,\beta'$-dimethylmuconic acid was added to a rubber composition in an identical manner disclosed in Example X. Results were substantially identical to those achieved in Example X.

EXAMPLE XII

The dihydrazide of cis-cis-$\alpha,\alpha',\beta$-trimethylmuconic acid was added to a rubber composition in substantially the identical manner as disclosed in Example X. The composition was then evaluated for Moony viscosity, aged in a circulating hot air oven as disclosed in Example X and then reevaluated for Moony viscosity. The results of antisouping stabilization in this example was substantially identical to those achieved in Example X.

EXAMPLE XIII

The dihydrazide of trans-trans-$\alpha,\beta,\beta'$-trimethylmuconic acid, the dihydrazide of cis-trans-$\alpha,\alpha',\beta,\beta'$-tetramethylmuconic acid each were separately compounded in a composition in an identical manner as that disclosed in Example X, with testing being carried out exactly as that disclosed in Example X. The results of inhibiting "souping" of rubber by the addition of these dihydrazides of dimethylmuconic acid were substantially identical to those results achieved in the compositions of Example X.

By the illustrations of the various dihydrazides of muconic acids given above, it is clearly demonstrated that the effectiveness of any of the dihydrazides of the various isomers of polymethylated muconic acids are useful as inhibitors of souping in unvulcanized oil extended rubber compositions.

As a means of illustrating another aspect of the present invention, viz., the use of dihydrazides of methylated muconic acids as plant growth regulators, the following example is given:

EXAMPLE XIV

Fifty grams of the dihydrazide of cis-cis-$\alpha,\alpha'$-dimethylmuconic acid were dissolved in 50 gallons of water and thereafter sprayed on one acre of three-week old tomato plants averaging four inches in height. Another acre of tomato plants at the same stage of growth and substantially the same height was sprayed at the same time with 20 gallons of water. The growing plants were observed for a 3-week period of time, after which measurements of the respective tomato plants in each of the respective plots were taken. The tomato plants in the plot treated with the dihydrazide of muconic acid averaged about five inches in height. The tomato plants in the untreated plot which were merely sprayed with water averaged over 7 inches in height. This demonstration illustrates the effect of the dihydrazide of dimethylmuconic acid in inhibiting the growth of growing tomato plants. Similar treatments to pepper plants, squash, cucumbers, watermelons and small fruits such as strawberries and raspberries were accomplished with equivalent results being obtained. Normally, an acre of plants requires about ten to fifty gallons of solution of the hydrazides of methylated muconic acid. The spray solution should contain 50 to a 1,000 parts per million of the dihydrazide of the methylated muconic acid to be effective as a plant growth retardant.

The dihydrazides of any of the methylated muconic acids disclosed hereinabove are equally effective in accomplishing the plant growth regulating achievements demonstrated in Example XIV given above. These dihydrazides can be applied in a single application such as that shown in the above example or can be applied at lesser rates by way of spaced time interval applications. At higher concentrations such as 300 to 500 parts per million of the dihydrazide of the methylated muconic acid in an aqueous solution, the hydrazides have been found effective as chemical pruning agents as well as dwarfing agents as shown above. An extremely high concentration of the dihydrazide of methylated muconic acids such as 500 to 1000 parts per million per 10 to 50 gallons of aqueous solution when applied to one acre has been found to be effective as a defoliant or a herbicide to specific broad leafed plants. The above solutions can be applied in standard agricultural spraying apparatus such as normally used in the treatment of agricultural plants. Also, the dihydrazides of methylated muconic acids can be dissolved in wax/oil emulsions used as plant antitranspirant compositions. For example, U.S. Pat. No. 3,410,678 issued Nov. 12, 1968 to Edward L. Ratledge discloses certain wax and oil-in-water emulsion compositions effective in the regulation of plant transpiration. It has been discovered that when the hydrazides of methylated muconic acids are dissolved in the plant transpiration regulation composition the double effect of transpiration regulation and growth regulation is accomplished.

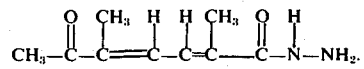

The invention claimed is:

1. Methylated muconic acid hydrazide of the formula